(12) United States Patent
Forcella

(10) Patent No.: US 12,427,238 B2
(45) Date of Patent: Sep. 30, 2025

(54) INNOVATIVE DEVICE FOR VASCULAR ACCESS IN A DIALYSIS TREATMENT

(71) Applicant: Mauro Fausto Angelo Forcella, Foggia (IT)

(72) Inventor: Mauro Fausto Angelo Forcella, Foggia (IT)

(*) Notice: Subject to any disclaimer, the term of this patent is extended or adjusted under 35 U.S.C. 154(b) by 486 days.

(21) Appl. No.: 17/797,522

(22) PCT Filed: Feb. 10, 2021

(86) PCT No.: PCT/IB2021/051059
§ 371 (c)(1),
(2) Date: Aug. 4, 2022

(87) PCT Pub. No.: WO2021/161176
PCT Pub. Date: Aug. 9, 2021

(65) Prior Publication Data
US 2023/0053637 A1  Feb. 23, 2023

(30) Foreign Application Priority Data
Feb. 11, 2020  (IT) .................. 102020000002707

(51) Int. Cl.
*A61M 1/36*  (2006.01)

(52) U.S. Cl.
CPC ... *A61M 1/3655* (2013.01); *A61M 2205/3331* (2013.01); *A61M 2205/3507* (2013.01)

(58) Field of Classification Search
CPC ........ A61M 1/3655; A61M 2205/3331; A61M 2205/3507; A61M 2205/3334; A61M 2205/8206; A61M 1/365; A61B 2017/111; A61B 2017/1132
See application file for complete search history.

(56) References Cited

U.S. PATENT DOCUMENTS

| | | | | |
|---|---|---|---|---|
| 9,056,171 B2 * | 6/2015 | Ward | | A61M 1/3655 |
| 2012/0059305 A1 * | 3/2012 | Akingba | | A61B 5/026 604/9 |
| 2012/0283617 A1 * | 11/2012 | Cull | | A61M 39/228 604/9 |
| 2014/0276345 A1 * | 9/2014 | Silin | | A61M 39/223 604/9 |

FOREIGN PATENT DOCUMENTS

EP  1072282 A1 *  1/2001  ............. A61B 17/12

* cited by examiner

*Primary Examiner* — Philip R Wiest
*Assistant Examiner* — Eric Rassavong
(74) *Attorney, Agent, or Firm* — R. Ruschena Patent Agent, LLC

(57) ABSTRACT

A device (100) for performing vascular access of the arteriovenous fistula type in a dialysis treatment comprising a first vertical branch (1), arterial, and a second vertical branch (2), venous, both branches being hollow and arranged parallel to each other while their lumens communicate via a horizontal branch (7). The device (100) comprises at least two blood flow interception means (10, 11) in which the first interception means (10) is arranged on the horizontal branch (7) and the second interception means (11) is disposed in a distal portion (2') of the second vertical branch (2), venous.

5 Claims, 2 Drawing Sheets

INNOVATIVE DEVICE FOR VASCULAR ACCESS IN A DIALYSIS TREATMENT

BACKGROUND OF THE INVENTION

1. Field of the Invention

The present invention relates to an innovative device for vascular access in a dialysis treatment. In particular, the device object of the present invention is able to minimise hemodynamic complications linked to common practices associated with dialysis treatment, that is, linked to difficulties in forming and maintaining vascular access.

2. Brief Description of the Prior Art

Chronic Kidney Disease (CKD) is defined as a clinical condition that has persisted for at least three months and is characterized by impaired kidney function and/or renal damage. According to the international guidelines issued by Kidney Disease Improving Global Outcomes (KDIGO), CKD is classified into 6 stages of increasing severity based on the degree of reduction in Glomerular Filtrate Rate (GFR) and the presence of albuminuria/proteinuria. The staging takes into account the different degrees of mortality risk and the evolution of CKD towards renal replacement treatment (dialysis or transplantation).

The causes leading to CKD are classically divided into glomerular, tubular and interstitial nephropathies. They are numerous but often remain unrecognized until renal function is irreversibly compromised. In fact, once established, CKD, regardless of the cause, progresses more or less slowly in most cases to the final stage of Uremia, a clinical condition that is incompatible with life and requires chronic treatment to replace renal function (dialysis or transplantation).

The functional unit of the kidney is the nephron, which is a small cluster of vessels through the wall of which excess water and metabolic waste products in the blood pass, resulting in the formation of urine. Each kidney contains approximately 1 million nephrons and can continue to maintain homeostasis until kidney damage exceeds 80%, the threshold at which clinical and laboratory signs of kidney failure appear. When the GFR falls below 15 ml/min, this leads to End-Stage Renal Disease (ESRD), a condition characterized by the destruction of more than 95% of the nephrons in which the kidney is no longer able to ensure the balance of the volume and composition of body fluids, resulting in a dangerous accumulation of water and the products of catabolism (toxins) in the blood.

ESRD is a condition that is incompatible with life and requires treatment to replace kidney function, which may be natural (kidney transplantation) or artificial (hemodialysis or peritoneal dialysis). The description of peritoneal dialysis and kidney transplantation will not be considered because this is beyond the scope of this discussion.

Hemodialysis is a complex therapeutic procedure, based on the physical principle of diffusion, which purifies the blood of uremic patients. The method uses equipment with peristaltic pumps that transport blood laden with toxic metabolites via a sterile extracorporeal circuit.

The nerve center of the entire system is the filter or dialyzer, which is a cylindrical chamber with a diameter of a few centimeters containing thousands of tubules with a diameter of the order of microns, which are in turn immersed in a liquid (dialysis bath) that is pumped from the equipment into the filter, in countercurrent to the direction of the blood. In the dialyzer, contact between the blood and the dialysis fluid occurs through a semi-permeable membrane that forms the wall of the microtubules. The passage through the semi-permeable membrane is very selective and only certain molecules are allowed to pass through, based on their chemical and physical characteristics and according to the principle of diffusion: in this system, toxins pass from the environment with the highest concentration (blood) to that with the lowest concentration (dialysis fluid), while substances that are useful to the body follow the opposite path.

The peristaltic pump, which sucks in the patient's toxin-laden blood and returns it purified and rich in useful substances, has an average flow rate of 300 ml/min, and since a standard dialysis session lasts 4 hours, the total amount of blood passing through the filter per treatment is approximately 72 liters. Taking into account that the amount of blood in the adult body is about 5 liters, it is processed about 15 times during the dialysis procedure as described above. It follows that the two needles that are placed in the patient's arm at each dialysis session, one for drawing blood and the other for returning it, must be inserted into blood vessels of a size that can guarantee such high flows. For this reason, every patient on a chronic hemodialysis program must have adequate vascular access to ensure the high blood flows required for artificial purification. There are three types of vascular access for hemodialysis: the arteriovenous fistula (AVF), the central venous catheter (CVC) and vascular prostheses. The international guidelines issued by the most important scientific societies agree that AVF is the vascular access of first choice because it is associated with an increase in survival with a marked improvement in quality of life and a longer duration with a lower risk of complications.

From a technical point of view, the setting up of an AVF for hemodialysis consists of surgically connecting a vein and an artery of the forearm in such a way as to short-circuit the high-pressure blood from the artery directly into the vein; in order to prevent part of the blood introduced into the vein from flowing back into the hand, the vein downstream of the anastomosis is generally ligated. This type of operation, which is usually done by anastomosing the radial artery with the forearm cephalic vein at wrist level, is technically called a distal lateral radiocephalic arteriovenous fistula. After surgery, within 3-4 weeks, the AVF matures: the high pressure of the blood column coming from the artery causes an increase in caliber and a thickening of the walls of the vein, a process called "vein arterialization", resulting in a considerable increase in the blood flow in the venous vessel, which becomes adequate to guarantee the high flow rates required by dialysis treatment.

However, as is well known, AVF carries different types of complications: intravascular, extravascular and hemodynamic. In particular, extravascular complications include aneurysms, pseudoaneurysms, and seromas, while hemodynamic complications are represented by "steal syndrome" and high-flow cardiac decompensation.

Specifically, aneurysms are dilations of an 'arterialized' section of vein whose diameter is twice that of the undilated part of the vessel; pseudoaneurysms are perivascular blood collections without their own wall, resulting from the rupture of the vessel wall, which retain a collar of communication with the vessel where there is a blood flow at speed (the greatest risk of aneurysms and pseudoaneurysms is given by the possibility of rupture); hematomas are perivascular blood collections that are not supplied. The risk of this type of complication is linked to the possibility of ab extrinsic compression with consequent obstruction of the access; seromas are serous liquid collections which are found more often in patients with vascular prostheses. The risk of seromas is mainly of an infectious nature; "steal syndrome" is an ischemic type of clinical picture affecting the distal parts of the limb that are the site of AVFs: in the most serious cases it is characterized by gangrenous lesions of the fingers that often require demolition of the necrotic extremities (it most frequently affects patients with proximal AVFs but is also increasing in those with distal AVFs due to the increase in the number of hemodialysis patients of advanced age, diabetics and those with peripheral vasculopathy).

The publication by Basile C. et al. showed that the presence of traditional risk factors added to the non-traditional risk factors typical of patients with CKD causes left ventricular hypertrophy (LVH) in 60% of uremic patients, even before starting dialysis. The publication by Stern et al. showed that the causes of high-flow heart failure include the presence of congenital or acquired AVF. Numerous other scientific works have long since demonstrated the close association between hemodialysis AVF and heart failure: Basile et al. showed that the risk of developing heart failure is higher in uremic patients with high-flow AVF and that cardiac changes can significantly regress after closure of the vascular access.

There is therefore a need to define an innovative device for AVF-type vascular access in dialysis treatment that can overcome the above-mentioned drawbacks and thus considerably simplify the surgical procedure for setting up the AVF, as well as reducing the extravascular complications associated with the use of the AVF.

SUMMARY OF THE INVENTION

The aim of the present invention is to minimize hemodynamic complications related to the use of AVF in patients undergoing dialysis, through the use of the device object of the present invention.

The innovative device is surgically implanted in the patient's forearm by full-channel anastomosing the four stumps of two vessels on the vertical branches after having transversally sectioned them.

The device is equipped with at least two diaphragms, which are activated (open or reduced) before starting the dialysis session, in order to ensure the high flows necessary for adequate blood purification and, at the end of the treatment, to maintain a minimum blood flow, variable from patient to patient, but such as to avoid thrombosis of the AVF and restore the physiological circulation of the upper limb.

Advantageously, an additional diaphragm of the device in question is capable of conveying the entire arterial flow into the "arterialized" vein so as to further increase the flow of blood available for purification.

Accordingly, the present invention defines an innovative device for setting up the AVF—type vascular access in a dialysis treatment, according to the independent product claim.

Further preferred and/or particularly advantageous ways of implementing the invention are described according to the features set out in the appended dependent claims.

BRIEF DESCRIPTION OF THE DRAWINGS

The invention will now be described with reference to the appended drawings, which illustrate some non-limiting implementation examples, wherein.

DETAILED DESCRIPTION OF THE INVENTION

Figure 1:
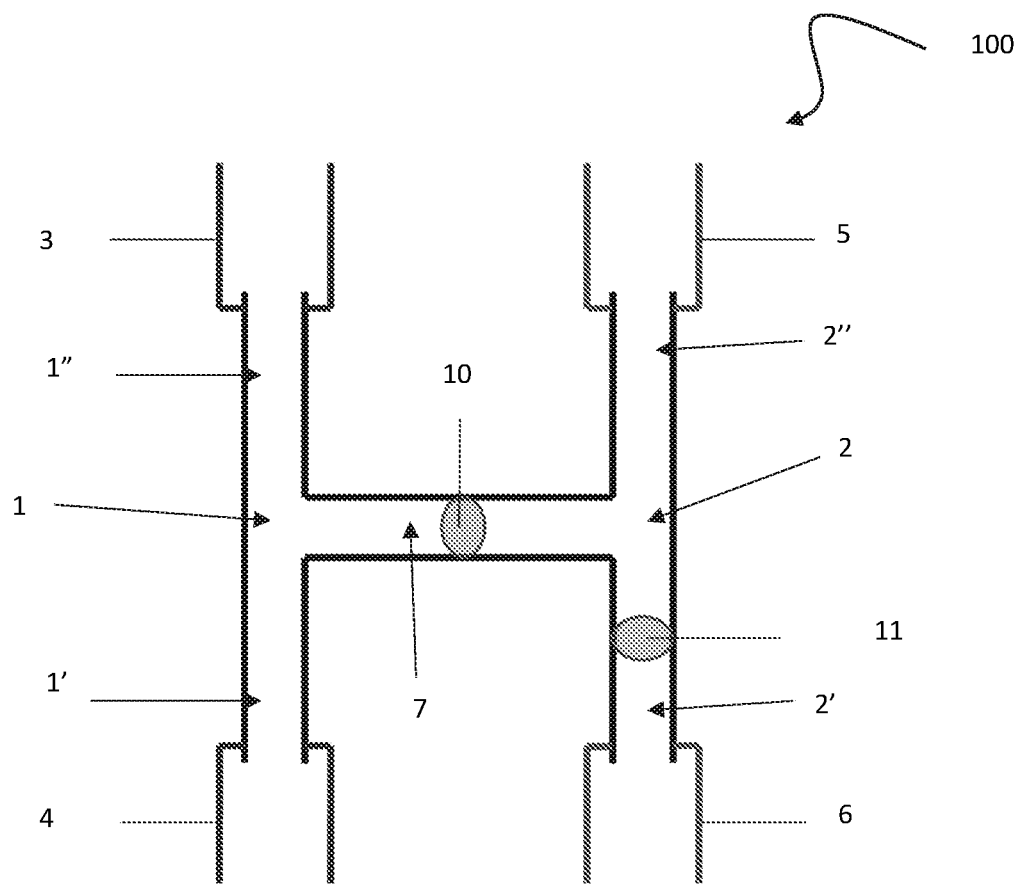
FIG. 1 shows a schematic of the device for performing dialysis, according to the present invention.
Figure 2:
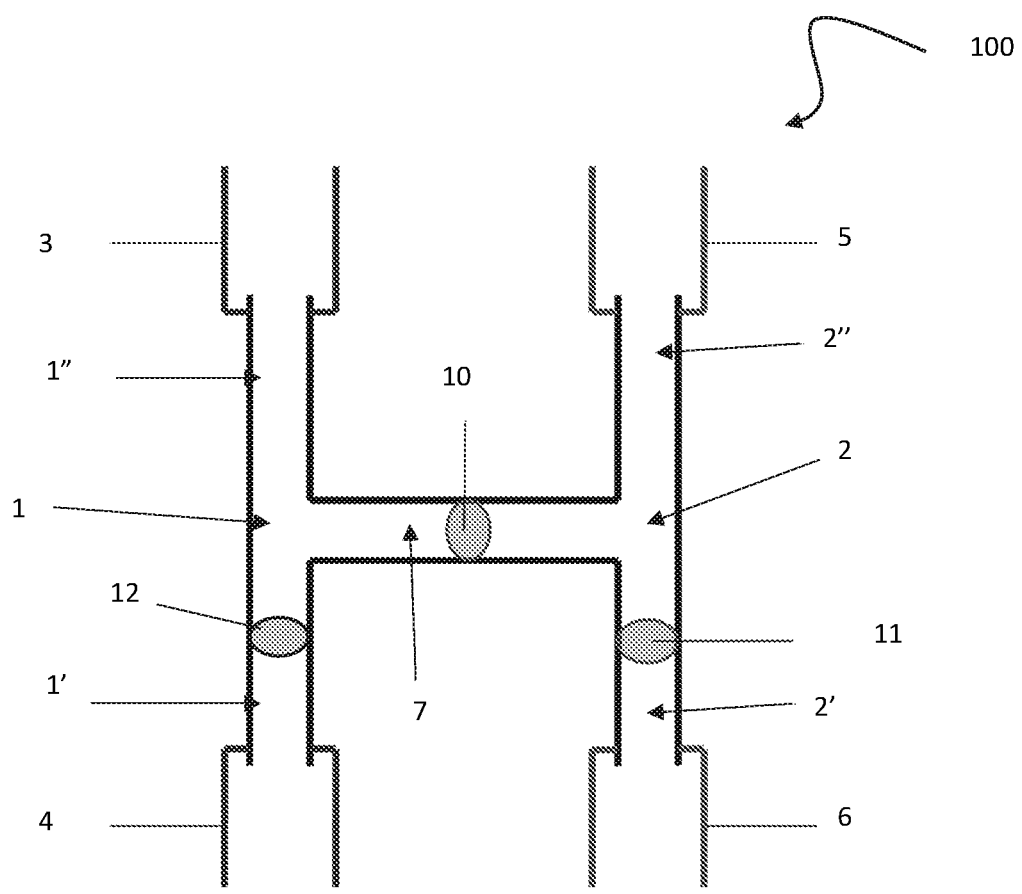
FIG. 2 shows a schematic diagram of the device for performing dialysis, according to a further embodiment of the present invention.

The invention relates to an innovative device 100 for vascular access in a dialysis treatment. As shown in FIG. 1, the device 100 has an almost "H" shape and comprises a first vertical branch 1 arterial and a second vertical branch 2 venous. Both branches are hollow and arranged parallel to each other while their lumens communicate via a horizontal branch 7. The vertical branches 1 and 2 comprise a distal portion 1', 2' and a proximal portion 1" and 2" respectively. The device 100 is constructed entirely of biocompatible material. It is surgically implanted in the patient's forearm by full-channel anastomosing the four stumps on the vertical branches 1 and 2: two stumps of the artery 3, 4 and two stumps of the vein 5 and 6, after transversely sectioning the two vessels. In particular, the distal portion 1' of the device 100 connects to the distal arterial stump 4 and the proximal portion 1" connects to the proximal arterial stump 3, while the distal portion 2' of the device 100 connects to the distal venous stump 6 and the proximal portion 2" connects to the proximal venous stump 5.

The device 100 further comprises at least two blood flow interception means or diaphragms: a first diaphragm 10 is arranged on the horizontal branch 7, in an almost median position and a second diaphragm 11 is arranged in the distal portion 2' of the venous branch 2.

Advantageously, the device is provided with a battery-operated electrical power supply means (of the type used for pace-makers) as well as with suitable actuating means so that the permeability of the diaphragms 10 and 11 can be adjusted from the outside by means of a remote control.

The diaphragms 10 and 11 of the horizontal branch 7 and the vertical venous branch 2 are operated before starting the dialysis session, opening diaphragm 10 and closing diaphragm 11, in order to ensure the high flows necessary for adequate blood purification. In other words, this operation allows the blood flow within the vein to be maximized during dialysis and restored to a more or less normal situation at the end of the dialysis treatment. This significantly reduces the risk of dialysis treatment complications and, at the same time, keeps the vascular access open for use in subsequent dialysis sessions. At the end of the treatment, diaphragm 10 is reduced in order to maintain a minimum blood flow, which varies from patient to patient, but which prevents thrombosis of the AVF, while diaphragm 11 of venous branch 2 is opened in order to restore physiological circulation of the upper limb.

According to a further embodiment of the present invention, the device 100 comprises a third diaphragm 12 arranged in the distal portion 1' of the arterial branch 1. Its closure, during the dialysis session, could serve to channel the entire arterial flow into the "arterialized" vein so as to further increase the flow rate of blood available for purification. This additional diaphragm 12 is therefore used in some patients in whom the arteriovenous fistula is also supplied by the ulnar artery, which normally supplies the hand. Diaphragm 12 is closed during dialysis treatment to prevent the loss of that portion of the blood supply to the hand via the ulnar artery. At the end of the treatment, the third diaphragm is opened in order to restore the physiological circulation of the upper limb.

Blood flow interceptors or diaphragms must also be made of highly biocompatible materials, similar to those used for heart valve prostheses, in order to minimise the possibility of thrombosis.

Advantageously, the system 100 provides a significant simplification of the AVF surgery. The AVF procedure is a vascular microsurgical procedure that requires a great deal of experience and dedication, so the number of nephrologists performing this type of interventional procedure is currently decreasing. In addition, the outcome of the procedure is burdened by great individual variability depending not only on the characteristics of the patient but also on the skill and experience of the nephrologist.

Therefore, the operation of transverse section of the vessels chosen for the AVF and the implantation of the device object of the present invention with full-channel anastomosis of the four vessel stumps, represents a simplification of the surgical procedure that can be easily performed by a nephrologist after a short training period or by a vascular surgeon, with consequent standardization of the surgical technique and of the outcomes and greater independence from the degree of experience of the operator.

Advantageously, device 100 allows a significant increase in flows and purification indexes. The possibility of obtaining, for a time limited to the duration of the dialysis session, very high blood flows make it possible to achieve optimal purification levels associated with increased survival and improved quality of life.

Advantageously, device 100 also allows the 'fistula first' program to be extended to heart patients and patients suffering from chronic obstructive pulmonary disease (COPD). As the device allows high flows for short periods of time (12 h/week or 7.1% of the total time) and restores physiological circulation in the remaining time (156 h/week or 93.1% of the total time), its use can also be extended to uremic patients with COPD and heart disease, who are currently excluded by their clinical condition from a AVF packaging program and dialyzed by the placement of CVC, the "second choice" vascular access, or started on peritoneal dialysis treatment.

Advantageously, device 100 achieves a significant reduction in extravascular complications associated with the use of AVF: aneurysms, pseudoaneurysms, hematomas. The extravascular complications of AVF are very frequent and often linked to accidental factors connected to the maneuvers of cannulation of the vessels and hemostasis after the hemodialysis session. The use of the device does not directly reduce the possibility of such complications occurring but certainly, by drastically reducing the flow in the arterialized venous vessel after the hemodialysis session, it determines a substantial modification of their evolution with spontaneous resolution in most cases: containment and reduced size of hematomas, slower growth of aneurysms and easier spontaneous closure of the collar of pseudoaneurysms. All this translates into a net reduction in hospitalizations due to complications of vascular access.

Advantageously, device 100 achieves a reduction in the hemodynamic complications associated with the use of AVF: 'steal syndrome' and high-flow heart failure. The use of device 100 restricted to the duration of the dialysis session and the subsequent immediate restoration of physiological circulation in the forearm leads to a drastic reduction in cases of "steal syndrome" and high-flow cardiac decompensation with a net reduction in mortality and improvement in the quality of life of uremic patients undergoing chronic hemodialysis treatment. All this translates into a net reduction in hospitalizations due to vascular access complications.

Advantageously, the device 100 allows the maintenance of vascular access (AVF) in the renal transplant patient. The ability to significantly reduce high venous return flows to the heart using the device allows vascular access to be maintained even after renal transplantation. For this reason, the nephrologist can choose, in agreement with the patient and listing the possible disadvantages and advantages, to maintain the vascular access, running the risk of developing a hemodynamic complication over time, or to close the AVF, giving up part of the patient's venous vascular heritage, who, in the event of a forced resumption of hemodialysis treatment, must necessarily undergo the construction of another vascular access. Restoring physiological forearm circulation by using the device can relieve nephrologist and patient of this difficult choice, preserving a "non-damaging" vascular access ready for use in case of resumption of dialysis treatment.

In addition to the methods of implementing the invention, as described above, it is to be understood that there are numerous further variants. It should also be understood that the above-described embodiments are merely illustrative and do not limit the subject matter of the invention, nor its possible applications or configurations. On the contrary, although the above description makes it possible for a person skilled in the art to implement the present invention at least according to an exemplary configuration thereof, it should be understood that numerous variations of the described components are conceivable, without thereby departing from the object of the invention as defined in the appended claims, interpreted literally and/or according to their legal equivalents.

The invention claimed is:

1. A device (100) for performing vascular access of an arteriovenous fistula (AVF) type in a dialysis treatment, said device (100) comprising:
   a first arterial vertical branch (1),
   a second venous vertical branch (2),
   both branches being hollow and arranged parallel to each other while their lumens communicate via a horizontal branch (7);
   at least two blood flow interception diaphragms (10, 11) wherein a first interception diaphragm (10) is arranged on the horizontal branch (7) and the second interception diaphragm (11) is disposed in a distal portion (2') of the second venous vertical branch (2);
   and wherein the diaphragms (10, 11) are configured to operate before starting a dialysis session, opening the first diaphragm (10) and closing the second diaphragm (11), to ensure a high flows necessary for adequate blood purification.

2. The device (100) according to claim 1, further comprising a third interception diaphragm (12) arranged in a distal portion (1') of the first arterial vertical branch (1);
   and wherein a closure of said third interception diaphragm (12), during a dialysis session, serves to channel an entire arterial flow into an "arterialized" vein so as to further increase a flow rate of blood available for purification and increase of purification indexes;
   and wherein said third interception diaphragm (12) is used for patients in whom the arteriovenous fistula (AVF) is also supplied by an ulnar artery, which normally supplies a body's hand;
   and wherein said interception diaphragm (12) is closed during dialysis treatment to prevent a loss of a portion blood supply to the hand via an ulnar artery; and when an end of a treatment is reached, said third interception diaphragm (12) is opened to restore a physiological circulation of an upper limb.

3. The device (100) according to claim 1, wherein said device (100) is surgically implanted in a patient's forearm and wherein the distal portion (1') of the first arterial vertical branch (1), is connected in use to a distal arterial stump (4) and a proximal portion (1") of the first arterial vertical branch (1), connects in use to a proximal arterial stump (3), while the distal portion (2') of the second venous vertical branch (2), connects in use to a distal venous stump (6) and a proximal portion (2") of the second venous vertical branch (2), connects in use to a proximal venous stump (5).

4. The device (100) according to claim 1, wherein said device (100) is entirely made of biocompatible material similar to a material used for heart valve prostheses, to minimize a possibility of thrombosis.

5. The device (100) according to claim 1, wherein said device (100) is provided with an electrical power supply and with an actuator device configured for regulating the blood flow interception device (10, 11), so that a permeability of the first interception diaphragms (10) and second interception diaphragm (11) can be adjusted from outside by means of a remote control.

\* \* \* \* \*